United States Patent [19]
Dowd et al.

[11] Patent Number: 5,507,813
[45] Date of Patent: Apr. 16, 1996

[54] SHAPED MATERIALS DERIVED FROM ELONGATE BONE PARTICLES

[75] Inventors: Michael Dowd, Bordentown; Denis G. Dyke, Long Branch, both of N.J.

[73] Assignee: Osteotech, Inc., Shrewsbury, N.J.

[21] Appl. No.: 164,152

[22] Filed: Dec. 9, 1993

[51] Int. Cl.$^6$ ................................ A61F 2/28; A61F 2/02
[52] U.S. Cl. ................................ 623/16; 623/11; 623/66
[58] Field of Search ................................ 623/1, 11, 12, 623/16, 18, 66; 424/422

[56] References Cited

U.S. PATENT DOCUMENTS

| | | |
|---|---|---|
| 3,739,773 | 6/1973 | Schmitt et al. . |
| 4,430,760 | 2/1984 | Smestad . |
| 4,440,750 | 4/1984 | Glowacki et al. . |
| 4,472,840 | 9/1984 | Jefferies . |
| 4,627,853 | 12/1986 | Campbell et al. . |
| 4,932,973 | 6/1990 | Gendler . |
| 5,053,049 | 10/1991 | Campbell . |
| 5,073,373 | 12/1991 | O'Leary et al. . |
| 5,092,887 | 3/1992 | Gendler . |
| 5,112,354 | 5/1992 | Sires . |
| 5,298,254 | 3/1994 | Prewett et al. . |
| 5,306,304 | 4/1994 | Gendler . |
| 5,314,476 | 5/1994 | Prewett et al. . |

FOREIGN PATENT DOCUMENTS

| | | |
|---|---|---|
| 0413492 | 2/1991 | European Pat. Off. . |
| 0419275 | 3/1991 | European Pat. Off. . |
| 0483944 | 5/1992 | European Pat. Off. . |
| 0495284 | 7/1992 | European Pat. Off. . |
| 0555807 | 8/1993 | European Pat. Off. . |
| 2175807 | 12/1986 | United Kingdom . |

OTHER PUBLICATIONS

Glowacki et al., Application of the Biological Principle of Induced Osteogenesis for Craniofacial Defects, The Lancet, pp. 959–962, 1981.

The Lancet vol. 1, No. 8227, May 2 1981, p. 959–962.

Kiviranta et al., "The Rate of Calcium Extraction During EDTA Decalcification from Thin Bone Slices as Assessed with Atomic Absorption Spectrophotometry", Histochemistry 68, pp. 119–127 (1980).

*Primary Examiner*—David Isabella
*Attorney, Agent, or Firm*—Dilworth & Barrese

[57] ABSTRACT

Surgically implantable shaped materials, e.g., sheets, are fabricated from elongate bone particles, advantageously those that have been demineralized. The materials when applied to a bone repair site enhance or accelerate new bone ingrowth by any one of a variety of biological and/or mechanical mechanisms.

21 Claims, No Drawings

SHAPED MATERIALS DERIVED FROM ELONGATE BONE PARTICLES

BACKGROUND OF THE INVENTION

This invention relates to surgically implanted materials fabricated from bone particles and, more particularly, to such materials which are made up of a coherent mass of elongate bone particles.

The use of demineralized bone powder in the repair of bone defects has been a subject of investigation for some time. Bone powder contains one or more substances, possibly bone morphogenic protein (BMP), which induce bone regeneration at the defect site. See, e.g., Covey et al., "Clinical Induction of Bone Repair with Demineralized Bone Matrix or a Bone Morphogenetic Protein", *Orthopaedic Review*, Vol. XVII, No. 8, pp. 857–863 (August, 1989). According to Habal et al., "Autologous Corticocancellous Bone Paste for Long Bone Discontinuity Defects: An Experimental Approach", *Annals of Plastic Surgery*, Vol. 15, No. 2, pp. 138–142 (Aug. 1985), autogenous bone which has been granulated into a pastelike material and combined with autogenous blood has been used in the repair of long bone defects in dogs.

U.S. Pat. No. 5,073,373 discloses a deformable, shape-sustaining osteogenic composition, suitable as a filler for osseous defects, in which particles of demineralized bone are uniformly distributed within a carrier which is a liquid polyhydroxy compound such as glycerol. The vast majority of the demineralized bone particles possess random, irregular geometries with an average median length to median thickness ratio of from about 1:1 to about 3:1.

Commonly assigned U.S. application Ser. No. 07/830,934 discloses a flowable osteogenic composition containing entangled demineralized bone particles of relatively high median length to median thickness ratio. The flowable osteogenic composition can possess a paste-like or putty-like consistency as well as a liquid or runny consistency.

SUMMARY OF THE INVENTION

It is an object of this invention to provide shaped materials fabricated from elongate bone particles and a process for making such materials.

It is another object of this invention to provide shaped materials fabricated from combinations of bone particles and one or more additives such as plasticizers, flexibilizing agents, biostatic/biocidal agents, fillers, binders, bonding agents, surface active agents, medically/surgically useful substances, and the like.

In keeping with these and related objects of this invention, a shaped material is provided which comprises a coherent mass of elongate bone particles.

The foregoing shaped material, e.g., in the form of a sheet, can be formed by applying a liquid slurry of elongate bone particles, e.g., filaments or fibers, to a porous support, draining excess liquid from the bone particles, optionally while applying a compressive force to the particles during and/or after drainage of the excess liquid, to provide a coherent, shaped wetted mass of bone particles and, optionally, drying the wetted mass. The material thus formed is relatively rigid when dry and, upon contact with a biocompatible liquid, e.g., water, saline solution, etc., becomes pliable and flexible.

Application of the foregoing shaped material to the site of a bone defect, e.g., one resulting from injury, infection, malignancy or developmental malformation, leads to new bone ingrowth by one or more biological mechanisms such as osteogenesis, osteoconduction and/or osteoinduction or by one or more physical mechanisms such as constituting a physical barrier to soft tissue ingrowth, providing a support or scaffolding for new bone growth, etc.

The term "osteogenic" as applied to the material of this invention shall therefore be understood as referring to the ability of the material of this invention to participate in the process of new bone growth regardless of the mechanism(s) involved.

The term "coherent" as applied to the mass of elongate bone particles refers to the ability of the bone particles to adhere to each other either mechanically, e.g., by entanglement, or by use of a biocompatible adhesive whether the shaped material containing the bone particles is in the dry or wetted, e.g., hydrated, state.

The term "shaped" as applied to the bone material of this invention shall be understood as referring to a determined or regular form or configuration, in contrast to an indeterminate or vague form or configuration (as in the case of a "lump" or other solid mass of no special form) and is characteristic of such materials as sheets, plates, disks, cones, pins, screws, and the like.

The term "rigid" shall be understood to refer to the relatively stiff, inflexible and somewhat brittle nature of the shaped materials of this invention while in the dry, i.e., unwetted, state.

The term "flexible" shall be understood to refer to the ability of the shaped material to become pliable upon being wetted or hydrated with a suitable biocompatible liquid and thus more readily conformable to a bone repair site.

DESCRIPTION OF THE PREFERRED EMBODIMENTS

The elongate bone particles employed in the shaped materials of this invention are generally characterized as having relatively high median length to median thickness ratios, e.g., at least about 50:1 and preferably at least about 100:1 and, similarly, relatively high median length to median width ratios, e.g., at least about 10:1 and preferably at least about 50:1. Such particles can be readily obtained by any one of several methods, e.g., by milling or shaving the surface of an entire bone or relatively large section of bone. Thereafter, the resulting elongate bone particles can be optionally demineralized as discussed herein.

Employing a milling technique, particles ranging in median length from about 2 up to about 200 mm or more (as in the case of the long bones), in median thickness from about 0.05 to about 2mm and in median width from about 1 to about 20mm can be readily obtained. Another procedure for obtaining the elongate bone particles herein, particularly useful for pieces of bone of up to about 100 mm in length, is the Cortical Bone Shredding Mill available from Os Processing Inc., 3303 Carnegie Avenue, Cleveland, Ohio 44115. Use of this bone mill results in the production of long, thin strips which quickly curl lengthwise to provide tubular-like bone particles.

Depending on the procedure employed for producing the elongate bone particles, one can obtain a mass of bone particles containing at least about 60 weight percent, preferably at least about 70 weight percent and most preferably at least about 80 weight percent of bone particles possessing a median length of from about 2 to about 200 mm or more and preferably from about 10 to about 100 mm, a median thickness of from about 0.05 to about 2 mm and preferably from about 0.2 to about 1 mm and a median width of from about 1 mm to about 20 mm and preferably from about 2 to about 5 mm. These bone particles can possess a median length to median thickness ratio of at least about 50:1 up to about 500:1 or more and preferably from about 50:1 to about 100:1 and a median length to median width ratio of from about 10:1 to about 200:1 and preferably from about 50:1 to about 100:1.

If desired, the mass of elongate bone particles can be graded into different sizes to reduce or eliminate any less desirable size(s) of particles which may be present. In overall appearance, the elongate bone particles can be described as filaments, fibers, threads, slender or narrow strips, etc. As already noted and depending on the manner in which they are produced, these elongate particles may have a tendency to curl to provide tubular-like particles. The bone particles can be obtained from cortical, cancellous and/or corticocancellous bone which may be of autogenous, allogenic and/or xenogeneic origin. Porcine bone is a particularly advantageous type of xenogeneic bone tissue which can be used as a source for the elongate demineralized bone particles of this invention.

Following the shaving, milling or other technique whereby they are obtained, the elongate bone particles are optionally subjected to demineralization in order to reduce their inorganic content to a low level, e.g., to not more than about 5% by weight of residual calcium and preferably to not more than about 0.5% by weight residual calcium. Demineralization of the bone particles will ordinarily 0 result in producing particles of slightly smaller dimensions.

The elongate bone particles can be demineralized in accordance with known and conventional procedures. In a preferred demineralization procedure, the elongate bone particles are subjected to a defatting/disinfecting step which is followed by an acid demineralization step. A preferred defatting/disinfectant solution is an aqueous solution of ethanol, the ethanol being a good solvent for lipids and the water being a good hydrophilic carrier to enable the solution to penetrate more deeply into the bone particles. The aqueous ethanol solution also disinfects the bone by killing vegetative microorganisms and viruses. Ordinarily at least about 10 to about 40 weight percent by weight of water (i.e., about 60 to about 90 weight percent of defatting agent such as alcohol) should be present in the defatting/disinfecting solution to produce optimal lipid removal and disinfection within the shortest period of time. The preferred concentration range of the defatting solution is from about 60 to about 85 weight percent alcohol and most preferably about 70 weight percent alcohol. Following defatting, the bone particles are immersed in acid over time to effect their demineralization. Acids which can be employed in this step include inorganic acids such as hydrochloric acid and organic acids such as peracetic acid. After acid treatment, the demineralized bone particles are rinsed with sterile water for injection to remove residual amounts of acid and thereby raise the pH. At this point some entanglement of the wet demineralized bone particles will result. The wet demineralized bone particles can then be immediately shaped into a shaped osteogenic material in accordance with the method of this invention or stored under aseptic conditions, advantageously in a lyophilized state, for processing at a later time.

The elongate bone particles can be admixed with one or more substances such as adhesives, fillers, plasticizers, flexibilizing agents, biostatic/biocidal agents, surface active agents, binding and bonding agents, fillers, and the like, prior to, during, or after shaping the particles into a desired configuration. Suitable adhesives, binding agents and bonding agents include acrylic resins, cellulosics, bioresorbable polymers such as polyglycolide, polylactide, glycolide-lactide copolymer, etc. Suitable fillers include bone powder, demineralized bone powder, hydroxyapatite, etc. Suitable plasticizers and flexibilizing agents include liquid polyhydroxy compounds such as glycerol, monacetin, diacetin, etc. Suitable biostatic/biocidal agents include antibiotics, povidone, sugars, etc. Suitable surface active agents include the biocompatible nonionic, cationic, anionic and amphoteric surfactants.

If desired, the bone particles can be modified in one or more ways, e.g., their protein content can be augmented or modified as described in U.S. Pat. Nos. 4,743,259 and 4,902,296. Any of a variety of medically and/or surgically useful substances can be incorporated in, or associated with, the bone particles either before, during or after fabrication of the shaped articles disclosed herein. Thus, e.g., one or more of such substances can be introduced into the demineralized bone particles, e.g., by soaking or immersing the bone particles in a solution or dispersion of the desired substance(s).

Medically/surgically useful substances which can be readily combined with the demineralized bone particles and/or osteogenic material of this invention include, e.g., collagen, insoluble collagen derivatives, etc., and soluble solids and/or liquids dissolved therein, e.g., antiviricides, particularly those effective against HIV and hepatitis; antimicrobials and/or antibiotics such as erythromycin, bacitracin, neomycin, penicillin, polymyxin B, tetracyclines, viomycin, chloromycetin and streptomycins, cefazolin, ampicillin, azactam, tobramycin, clindamycin and gentamicin, etc.; biocidal/biostatic sugars such as dextroal, glucose, etc.; amino acids, peptides, vitamins, inorganic elements, co-factors for protein synthesis; hormones; endocrine tissue or tissue fragments; synthesizers; enzymes such as collagenase, peptidases, oxidases, etc.; polymer cell scaffolds with parenchymal cells; angiogenic drugs and polymeric carriers containing such drugs; collagen lattices; antigenic agents; cytoskeletal agents; cartilage fragments, living cells such as chondrocytes, bone marrow cells, mesenchymal stem cells, natural extracts, tissue transplants, bone, demineralized bone powder, autogenous tissues such blood, serum, soft tissue, bone marrow, etc.; bioadhesives, bone morphogenic proteins (BMPs), transforming growth factor (TGF-beta), insulin-like growth factor (IGF-1); growth hormones such as somatotropin; bone digestors; antitumor agents; immuno-suppressants; permeation enhancers, e.g., fatty acid esters such as laureate, myristate and stearate monoesters of polyethylene glycol, enamine derivatives, alpha-keto aldehydes, etc.; and, nucleic acids. The amounts of such optionally added substances can vary widely with optimum levels being readily determined in a specific case by routine experimentation.

To prepare the shaped osteogenic materials of this invention, a quantity of elongate bone particles, preferably those that have been demineralized, slurried in a suitable liquid, e.g., water, organic protic solvent, aqueous solution such as physiological saline, etc., and optionally containing one or more biocompatible ingredients such as adhesives, fillers, plasticizers, flexibilizing agents, biostatic/biocidal agents, surface active agents, medically/surgically useful substances, etc., as previously described, is applied to a form such as a flat sheet, mesh screen or three-dimensional mold and excess liquid is removed, e.g., by being drained away. This procedure is referred to herein as "wet-laying". For example, in the case of a sheet, the thickness of the layer of wetted bone particles can vary widely, e.g., from about 1 to about 40 mm. Some particle entanglement results from the wet-laying operation. Further particle entanglement, if necessary or desirable, can be effected by the use of water jets or other suitable mechanical entangling methods. Either before or after the wet-laying procedure, one or more additional substances can be added to the bone particles, e.g., thixotropic agents, therapeutic agents, and the like, as previously mentioned. The wet demineralized bone particles are then dried either in an oven at a temperature of from about 30° to about 70° C., preferably from about 30° to about 40° C., or by lyophilization in accordance with procedures and conditions that are well known in the art, e.g., a shelf temperature of from about −20° to about −35° C., a vacuum of from about 150 to about 100 mTorr for a time of from about 4 to about 48 hours depending on the mass. In an alternative embodiment herein, the entangled mass of bone particles can be subjected to a compressive force, e.g., of up to about 100 psi, during and/or after the wet-laying step and/or while the drained but still wet shaped article is being dried. The resulting shaped material is rigid and relatively strong when dry and flexible and pliable when wetted or hydrated.

At the site of implantation, the shaped article can be employed in the dry state or, where site conformation is desired, in the hydrated state. The dry or hydrated article can be cut or sized if need be to conform to a site being repaired. The article can be hydrated with a suitable biocompatible liquid, e.g., water, saline solution, etc., for a period of time ranging from about 1 to about 120 minutes depending on the density of the shaped material. After being hydrated, the shaped material becomes flexible yet retains its shape and much of its strength. The shaped material of this invention can be packaged in either the dried or wet state and stored for subsequent application. In some circumstances, it is preferable to package the material in the wet state so that it is ready for immediate use at the surgical site.

The shaped materials of this invention can be utilized in a wide variety of orthopaedic, neurosurgical and oral and maxillofacial surgical procedures such as the repair of simple and compound fractures and non-unions, external and internal fixations, joint reconstructions such as arthrodesis, general arthroplasty, cup arthroplasty of the hip, femoral and humeral head replacement, femoral head surface replacement and total joint replacement, repairs of the vertebral column including spinal fusion and internal fixation, tumor surgery, e.g. deficit filling, discectomy, laminectomy, excision of spinal cord tumors, anterior cervical and thoracic operations, repair of spinal injuries, scoliosis, lordosis and kyphosis treatments, intermaxillary fixation of fractures, mentoplasty, temporomandibular joint replacement, alveolar ridge augmentation and reconstruction, inlay bone grafts, implant placement and revision, sinus lifts, etc. These materials can be sutured or stapled in place for anchoring purposes and serve in guided tissue regeneration or as barrier materials.

The following examples are illustrative of the preparation of composition containing elongate demineralized bone particles and the fabrication of a shaped sheet material from the composition.

EXAMPLE 1

A section of allogenic cortical bone approximately 9 cm long and 10–30 mm wide was placed in the hopper of a Cortical Bone Shredding Mill of Os Processing, Inc., 3303 Carnegie Avenue, Cleveland, Ohio 44115 equipped with a 20-flute rotary cutter. The mill was operated at a speed of about 120 rpm until approximately 100 to 1000 g of mass of bone particles of which at least 80 weight percent was made up of particles having a median length of about 10 mm and a median thickness of about 0.5 mm was obtained. The elongate bone particles were then placed in a reactor. A 70 weight percent ethanol solution at a rate of 30 milliliters per gram of bone particles was introduced into the reactor followed by agitation for 1 hour (Bolander et al., *Journal of Bone and Joint Surgery*, Vol. 68-A, No. 8 (Oct. 1986)) to effect defatting and disinfecting of the bone particles. Following drainage of the ethanol, a 0.6N solution of HCl at 15 ml per gram of bone was introduced into the reactor (Bolander et al., supra), the reaction proceeding for 3 hours (Glowackie, *AATB Workshop*, 11th Annual meeting (1987). Following drainage of the HCl the bone particles were covered and rinsed three times with water for injection (WFI) with the WFI being replaced at 5 minute intervals. Following drainage of the WFI, the bone particles were completely covered with 0.1M sodium phosphate, a procedure which was repeated until the pH of the solution fell between 6.8 and 7.4. The rinsing procedure with WFI was repeated to provide a composition containing wet demineralized, elongate bone particles containing not more than about 0.5 weight percent residual calcium.

EXAMPLE 2

A quantity of the composition containing wet demineralized bone particles from Example 1 was spread out on a tight-mesh screen to a depth of 10mm to form a flat sheet with dimensions of 5 inches by 5 inches while excess liquid drained off through the screen. The entire surface was subjected to about 8psi and the load was maintained while the sheet was oven-dried. The resultant rigid sheet was approximately 5 mm in depth, brittle to some extent, and had significant tensile strength. A 2 inch by 2 inch portion of the sheet was cut off with scissors and immersed in water for injection for 15 minutes. The sheet approximately doubled in thickness after this time. The piece was now significantly more pliable and could be bent in a circular fashion so that the opposite sides met. The integrity of the structure was not visibly affected by this bending and the piece returned to its original shape upon release. A sheet material which is more pliable or less pliable can be accomplished by changing the initial thickness of the particles during the wet-lay process or by varying the compression force.

EXAMPLE 3

The hydrated sheet of Example 2 is applied to an osseous defect site using an instrument such as forceps. The ability of the foregoing shaped material to maintain its shape and position in the aqueous environment of the body is superior to a like quantity of demineralized bone powder.

What is claimed is:

1. A shaped material comprising a coherent mass of elongate, mechanically entangled demineralized bone particles wherein at least about 60 weight percent of the bone particles possess a median length of from about 10 mm to about 100 mm, a median thickness of from about 0.02 mm to about 1 mm and a median width of from about 2 mm to about 5 mm.

2. The shaped material of claim 1 exhibiting osteogenic activity.

3. The shaped material of claim 1 wherein the bone particles are obtained from cortical, cancellous and cortico-cancellous bone of autogenous allogenic and xenogenic origin.

4. The shaped material of claim 1 wherein the bone particles are obtained from porcine bone.

5. The shaped material of claim 1 further comprising one or more additives selected from the group consisting of plasticizers, flexibilizing agents, biostatic agents, biocidal agents, surface active agents, binding and bonding agents and fillers.

6. The shaped material of claim 1 further comprising at least one additional ingredient selected from the group consisting of antiviral agent, antimicrobial agent, antibiotic agent, amino acid, peptide, vitamin, inorganic element, protein synthesis co-factor, hormone, endocrine tissue, synthesizer, enzyme, polymer-cell scaffolding agent with parenchymal cells, angiogenic drug, demineralized bone powder, collagen lattice, antigenic agent, cytoskeletal agent, mesenchymal stem cells, bone digester, antitumor agent, cellular attractant, fibronectin, growth hormone cellular attachment agent, immunosuppressant, nucleic acid, hydroxy apatite and penetration enhancer.

7. The shaped material of claim 1 in the form of a flat sheet, curved sheet, plate, disk, cone, pin, screw or tube.

8. A shaped material comprising a coherent mass of elongate, mechanically entangled demineralized bone particles wherein at least about 60 weight percent of the bone particles possess a median length to median thickness ratio of from about 50:1 to about 500:1 and a median length to median width ratio of from about 10:1 to about 200:1.

9. The shaped material of claim 8 exhibiting osteogenic activity.

10. The shaped material of claim 8 wherein the bone particles are obtained from cortical, cancellous and cortico-cancellous bone of autogenous allogenic and xenogenic origin.

11. The shaped material of claim 8 wherein the bone particles are obtained from porcine bone.

12. The shaped material of claim 8 further comprising one or more additives selected from the group consisting of plasticizers, flexibilizing agents, biostatic agents, biocidal agents, surface active agents, binding and bonding agents and fillers.

13. The shaped material of claim 8 further comprising at least one additional ingredient selected from the group consisting of antiviral agent, antimicrobial agent, antibiotic agent, amino acid, peptide, vitamin, inorganic element, protein synthesis cofactor, hormone, endocrine tissue, synthesizer, enzyme, polymer-cell scaffolding agent with parenchymal cells, angiogenic drug, demineralized bone powder, collagen lattice, antigenic agent, cytoskeletal agent, mesenchymal stem cells, bone digester, antitumor agent, cellular attractant, fibronectin, growth hormone cellular attachment agent, immunosuppressant, nucleic acid, hydroxy apatite and penetration enhancer.

14. The shaped material of claim 1 in the form of a flat sheet, curved sheet, plate, disk, cone, pin, screw or tube.

15. A shaped material comprising a coherent mass of elongate, mechanically entangled, demineralized bone particles wherein at least about 60 weight percent of the bone particles possess a median length to median thickness ratio of from about 50:1 to about 100:1 and a median length to median width ratio of from about 50:1 to about 100:1.

16. The shaped material of claim 15 exhibiting osteogenic activity.

17. The shaped material of claim 15 wherein the bone particles are obtained from cortical, cancellous and cortico-cancellous bone of autogenous allogenic and xenogenic origin.

18. The shaped material of claim 15 wherein the bone particles are obtained from porcine bone.

19. The shaped material of claim 15 further comprising one or more additives selected from the group consisting of plasticizers, flexibilizing agents, biostatic agents, biocidal agents, surface active agents, binding and bonding agents and fillers.

20. The shaped material of claim 15 further comprising at least one additional ingredient selected from the group consisting of antiviral agent, antimicrobial agent, antibiotic agent, amino acid, peptide, vitamin, inorganic element, protein synthesis cofactor, hormone, endocrine tissue, synthesizer, enzyme, polymer-cell scaffolding agent with parenchymal cells, angiogenic drug, demineralized bone powder, collagen lattice, antigenic agent, cytoskeletal agent, mesenchymal stem cells, bone digester, antitumor agent, cellular attractant, fibronectin, growth hormone cellular attachment agent, immunosuppressant, nucleic acid, hydroxy apatite and penetration enhancer.

21. The shaped material of claim 15 in the form of a flat sheet, curved sheet, plate, disk, cone, pin, screw or tube.

* * * * *